(12) United States Patent
Hosogoe (10) Patent No.: US 10,695,029 B2
(45) Date of Patent: Jun. 30, 2020

(54) ULTRASONIC ENDOSCOPE

(71) Applicant: HOYA CORPORATION, Tokyo (JP)

(72) Inventor: Yoshitsugu Hosogoe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 204 days.

(21) Appl. No.: 15/511,372

(22) PCT Filed: Oct. 6, 2016

(86) PCT No.: PCT/JP2016/079771
§ 371 (c)(1),
(2) Date: Mar. 15, 2017

(87) PCT Pub. No.: WO2017/061537
PCT Pub. Date: Apr. 13, 2017

(65) Prior Publication Data
US 2017/0290566 A1    Oct. 12, 2017

(30) Foreign Application Priority Data

Oct. 8, 2015    (JP) .................................. 2015-200036

(51) Int. Cl.
*A61B 8/00* (2006.01)
*A61B 8/12* (2006.01)
(Continued)

(52) U.S. Cl.
CPC .......... *A61B 8/445* (2013.01); *A61B 1/00078* (2013.01); *A61B 1/00098* (2013.01);
(Continued)

(58) Field of Classification Search
None
See application file for complete search history.

(56) References Cited

U.S. PATENT DOCUMENTS 9,380,996 B2 *  7/2016  Hiraoka ................. A61B 8/445
2015/0173711 A1   6/2015  Hiraoka
2016/0183914 A1   6/2016  Fujimura

FOREIGN PATENT DOCUMENTS

| JP | 2002-360577 | 12/2002 |
| JP | 2013-233210 | 11/2013 |

(Continued)

*Primary Examiner* — Carolyn A Pehlke
*Assistant Examiner* — Marjan Saboktakin
(74) *Attorney, Agent, or Firm* — Greenblum & Berstein, P.L.C.

(57) ABSTRACT

In a rigid distal end portion of an ultrasonic endoscope, a side-viewing optical observation portion and a wave transmission/reception face of an ultrasonic probe are provided on respective sides, in the width direction, of a boundary side wall of a pair of side walls constituting a laterally open recess. The wave transmission/reception face is arranged in a range in which at least a part of the wave transmission/reception face overlaps the boundary side wall, while being offset from an elevator in the longitudinal direction of an insertion portion. When the rigid distal end portion is viewed in an observation direction of the optical observation portion, a top portion of the elevator is located on a line connecting a center of the outer shape of the wave transmission/reception face of the ultrasonic probe, and a center, in the width direction, of the distal end connecting portion of a treatment tool conduit.

3 Claims, 6 Drawing Sheets

(51) Int. Cl.
*A61B 1/06* (2006.01)
*A61B 1/00* (2006.01)
*A61B 1/018* (2006.01)
*A61B 5/00* (2006.01)

(52) U.S. Cl.
CPC .......... *A61B 1/00177* (2013.01); *A61B 1/018* (2013.01); *A61B 1/0615* (2013.01); *A61B 8/12* (2013.01); *A61B 5/0084* (2013.01)

(56) References Cited

FOREIGN PATENT DOCUMENTS

| | | |
|---|---|---|
| JP | 2014-239734 | 12/2014 |
| WO | 2014/038638 | 3/2014 |
| WO | 2015/053044 | 4/2015 |

* cited by examiner

ULTRASONIC ENDOSCOPE

TECHNICAL FIELD

The present invention relates to an ultrasonic endoscope, and particularly to a side-viewing ultrasonic endoscope that is appropriate for examining a change in the biliary tract (biliary duct).

BACKGROUND ART

Ultrasonic endoscopes that can perform both endoscopic retrograde cholangiopancreatography (ERCP) and endoscopic ultrasound-guided fine needle aspiration (FNA) have been proposed. Ultrasonic endoscopes of this type are each provided with, in a rigid distal end portion located at the distal end of an insertion portion to be inserted into the body, a side-viewing optical observation portion, an ultrasonic probe, and an opening of a treatment tool conduit (instrument channel). Flexible linear treatment tools such as a puncture needle and a contrast tube are selected based on a treatment to be executed, and are inserted into the treatment tool conduit to protrude from the opening. An elevator for changing the direction in which the flexible linear treatment tools protrude is provided in the opening of the treatment tool conduit.

PRIOR ART DOCUMENT

Patent Documents

Patent Document 1: JP 2014-239734A
Patent Document 2: JP 2013-233210A

SUMMARY OF INVENTION

Technical Problem

Although the ultrasonic endoscopes of Patent Documents 1 and 2 differ from each other in the position at which an opening of a treatment tool conduit is set, both have a configuration in which an ultrasonic probe is added to a rigid distal end portion of a side-viewing endoscope in the longitudinal direction (axial direction) of an insertion portion, and thus there is the problem that the rigid distal end portion tends to be long. A long rigid distal end portion affects the insertion operability when the endoscope is used, and it is difficult for the endoscope to pass particularly through a bent part such as the duodenum. If the ultrasonic probe is arranged parallel to the opening of the treatment tool conduit in a direction (radial direction of the insertion portion) that is orthogonal to the longitudinal direction of the insertion portion, the length in the insertion axial direction of the rigid distal end portion is suppressed, but the diameter of the rigid distal end portion is too large, or it is difficult for the puncture needle to protrude into an ultrasonic scan plane of the ultrasonic probe.

In order to solve the above-described problems, it is an object of the present invention to provide an ultrasonic endoscope in which a rigid distal end portion is reduced in length without impairing operability.

Solution to Problem

The present invention is directed to an ultrasonic endoscope of a type in which a rigid distal end portion of an insertion portion is provided with an optical observation portion, a laterally open recess that has an elevator in the inside thereof, and an ultrasonic probe. The optical observation portion is of a side-viewing type in which an objective window is directed to a side in an observation direction that is substantially orthogonal to a longitudinal direction of the insertion portion. The laterally open recess is open in the same direction as the observation direction of the optical observation portion, and has a pair of side walls that are separated from each other in a width direction that is substantially orthogonal to the longitudinal direction of the insertion portion and the observation direction. A distal end connecting portion of a treatment tool conduit that is arranged in the insertion portion is connected to the laterally open recess, and a treatment tool inserted into the treatment tool conduit can protrude from the opening of the laterally open recess. The elevator is supported in the laterally open recess so as to be able to perform rising/falling operation around a shaft directed in the width direction, and sets a direction in which the treatment tool protrudes from the laterally open recess, using a top portion of the elevator that protrudes the most in the observation direction. The ultrasonic probe is configured to obtain an ultrasonic tomographic image via a wave transmission/reception face that comes into contact with a part to be observed. According to the present invention, these constituent components of the rigid distal end portion of the ultrasonic endoscope are arranged as follows. First, with respect to the width direction, the optical observation portion is located on one side, of a boundary side wall that is one of the pair of side wall of the laterally open recess, and the wave transmission/reception face of the ultrasonic probe is located on the opposite side. Also, with respect to the longitudinal direction, the wave transmission/reception face of the ultrasonic probe is located in a range in which at least a part of the wave transmission/reception face overlaps the boundary side wall of the laterally open recess, while being offset from the elevator. Furthermore, when the rigid distal end portion is viewed from the side in the observation direction, the top portion of the elevator is located on a virtual line that connects a center of an outer shape of the wave transmission/reception face of the ultrasonic probe, and a center, in the width direction, of the distal end connecting portion of the treatment tool conduit.

The center of the outer shape of the wave transmission/reception face of the ultrasonic probe and the center, in the width direction, of the distal end connecting portion of the treatment tool conduit may be arranged such that the virtual line that connects both of the centers to each other may be directed substantially parallel to the longitudinal direction of the insertion portion, or may intersect the longitudinal direction of the insertion portion.

Advantageous Effects of Invention

The ultrasonic endoscope of the present invention employs an arrangement in which at least a part of the wave transmission/reception face of the ultrasonic probe overlaps the boundary side wall of the laterally open recess in the longitudinal direction of the insertion portion (they are parallel to each other in the width direction of the insertion portion), and thus it is possible to obtain an effect of suppressing the length in the longitudinal direction of the rigid distal end portion including the ultrasonic probe. Because the ultrasonic probe has a relationship to the elevator in which they are not parallel to each other in the width direction of the insertion portion, it is also possible to suppress an increase in the dimension in the width direction of the rigid distal end portion. Furthermore, when the rigid distal end portion is viewed from a side in the observation direction, the top portion of the elevator is located on the virtual line that connects the center of the wave transmission/reception face of the ultrasonic probe, and the center, in the width direction, of the distal end connecting portion of the treatment tool conduit, and thus it is possible to cause a treatment tool such as a puncture needle to reliably protrude into the scan plane of the ultrasonic probe. Accordingly, it is possible to realize an ultrasonic endoscope that achieves both improvement in insertability and excellent operability, due to a rigid distal end portion being downsized (in particular, reduced in the longitudinal direction thereof).

DESCRIPTION OF EMBODIMENTS

Figure 1:
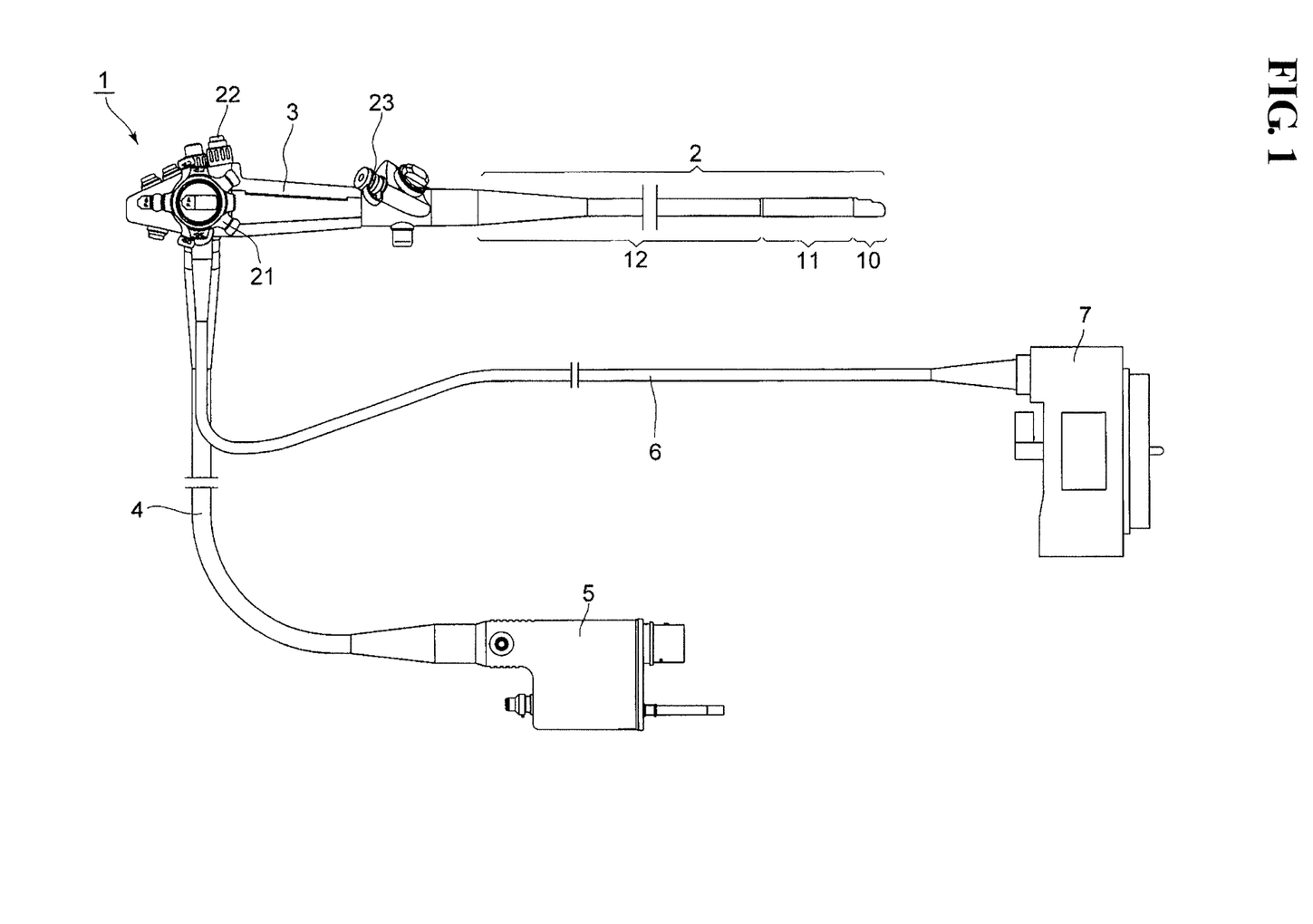
FIG. 1 is a diagram illustrating an overall configuration of an ultrasonic endoscope to which the present invention is applied.

Hereinafter, embodiments of the present invention will be described with reference to the drawings. FIG. 1 shows an overall configuration of an ultrasonic endoscope 1 to which the present invention is applied. The ultrasonic endoscope 1 is provided with: a narrow-diameter insertion portion 2 that is to be inserted into the body of a patient; an operation portion 3 that is connected to the base of this insertion portion 2; a video connector 5 that is provided at a distal end of a universal tube 4 extending from the operation portion 3; and an ultrasonic signal connector 7 that is provided at a distal end of a cable 6 extending from the operation portion 3, the cable 6 being separate from the universal tube 4.

The insertion portion 2 includes, in order from the front side (in the order of insertion into the body of the patient), a rigid distal end portion 10, a bending portion 11 that is configured to be bent by being remotely controlled using the operation portion 3, and a flexible tube 12 having flexibility. The operation portion 3 is provided with an operation knob 21 for bending the bending portion 11, a suction button 22 to start suction from a suction opening of the rigid distal end portion 10 (a distal end connecting portion 40a of a treatment tool conduit 40 that will be described later), a treatment tool insertion opening 23 that serves as an entrance of the treatment tool conduit 40 that will be described later, and the like.

Figure 2:
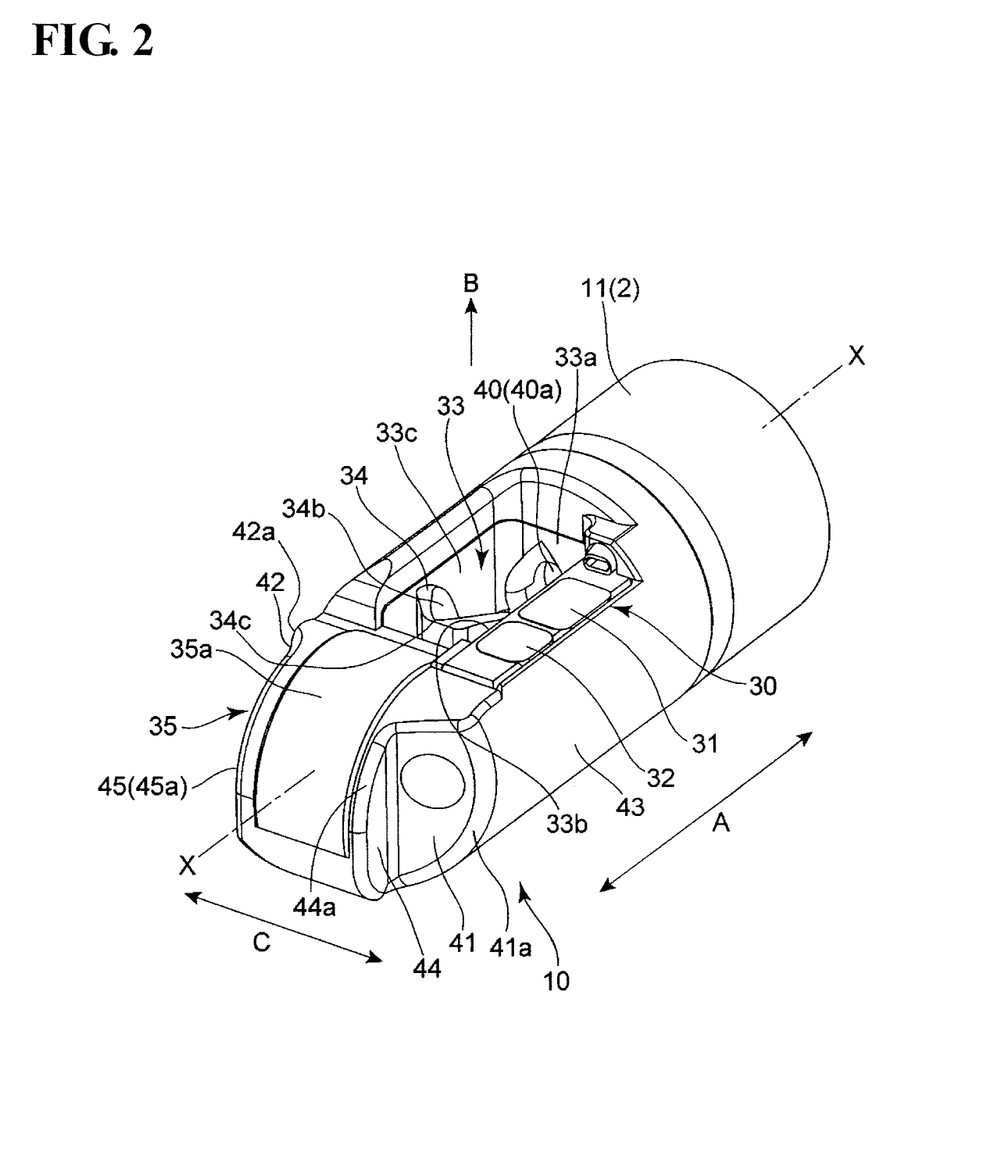
FIG. 2 is a perspective view of a rigid distal end portion of an insertion portion of the ultrasonic endoscope of FIG. 1.
Figure 3:
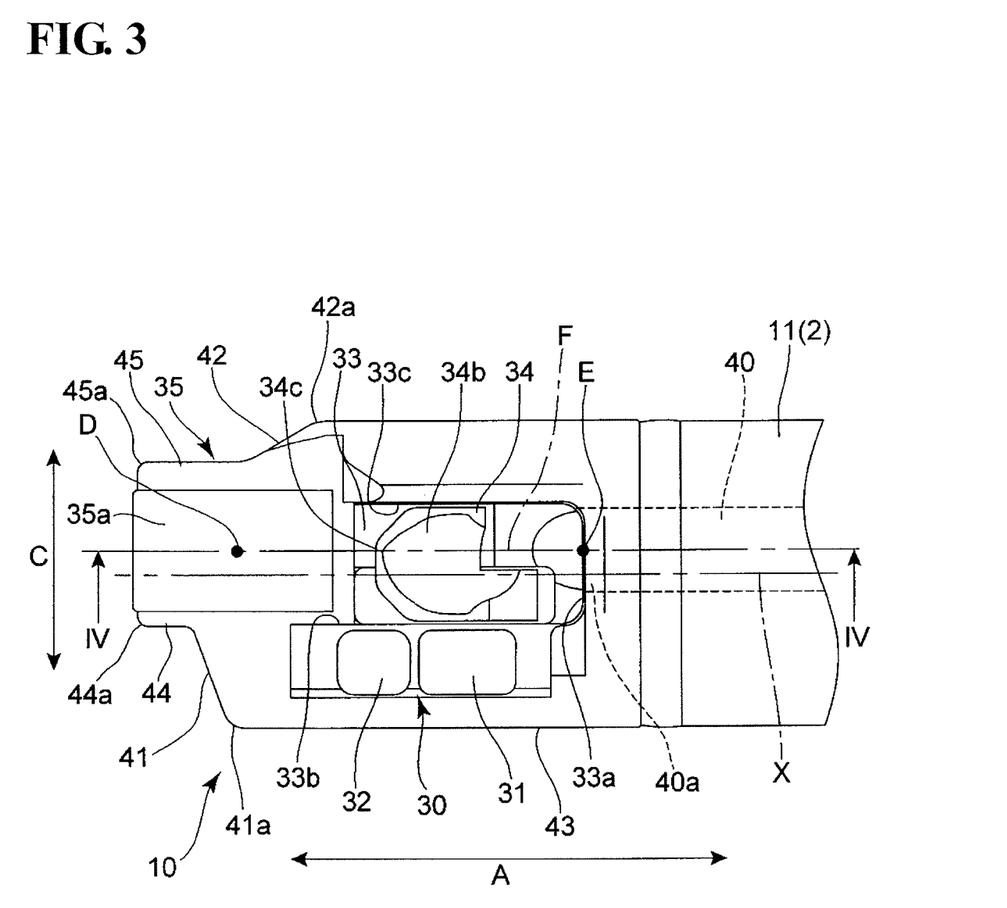
FIG. 3 is a plan view of the rigid distal end portion when viewed from a side in a direction in which observation is performed using an optical observation portion.

A detailed configuration of the rigid distal end portion 10 is shown in FIGS. 2 to 5. An arrow A in the drawings indicates a longitudinal direction (insertion axial direction) of the insertion portion 2. A dashed-dotted line X in the drawings indicates a central axis that extends in the longitudinal direction A passing through the center in the radial direction of the cylindrical insertion portion 2. The ultrasonic endoscope 1 is a side-viewing endoscope in which an objective window 31 and an illumination window 32, which constitute an optical observation portion 30, are directed in a direction (radial direction of the rigid distal end portion 10) that is substantially orthogonal to the longitudinal direction A. An arrow B in FIGS. 2, 4, and 5 indicates a direction (side-viewing direction) in which an optical system performs observation via the objective window 31. FIG. 3 is a plane view of the rigid distal end portion 10, showing the fronts of the objective window 31 and the illumination window 32 from the side in the observation direction B (on the axis extending in the observation direction B). A width direction C of the rigid distal end portion 10 is the radial direction of the insertion portion 2 that is substantially orthogonal to both of the longitudinal direction A and the observation direction B (FIGS. 2 and 3).

The objective window 31 and the illumination window 32 are arranged side by side in the longitudinal direction A at positions that are offset from the central axis X in the width direction C. An observation optical system and an image sensor unit that are not shown are provided in the rigid distal end portion 10, and an objective lens constituting the observation optical system is located behind the objective window 31. The observation optical system can observe an area lateral to the rigid distal end portion 10 via the objective window 31 that is directed in the observation direction B, and the image sensor unit photoelectrically converts an image obtained by the observation optical system. An image signal cable (not shown) is connected to the image sensor unit, is guided to the universal tube 4 from the insertion portion 2 via the operation portion 3 (see FIG. 1), and is connected to a video processor (not shown) via the video connector 5. As a result of the video processor processing image signals transmitted through the image signal cable, an image is displayed and recorded.

In addition to the image signal cable, a light guide fiber bundle (not shown) is arranged in the ultrasonic endoscope 1. An incident-side end of the light guide fiber is connected to the video processor via the video connector 5, and illumination light is incident on the light guide fiber from a light source device (not shown) provided in the video processor. An exit-side end of the light guide fiber is located behind the illumination window 32 of the rigid distal end portion 10, and illumination light can be distributed to the side of the rigid distal end portion 10 via the illumination window 32.

The rigid distal end portion 10 is provided with, in addition to the objective window 31 and the illumination window 32 of the optical observation portion 30, a laterally open recess 33, an elevator 34, and an ultrasonic probe 35. As shown in FIGS. 2 and 3, the laterally open recess 33 is formed at a position adjacent to the optical observation portion 30 in the width direction C, and is open in the observation direction B. The laterally open recess 33 has a rear wall 33a that is substantially orthogonal to the longitudinal direction A, and a side wall 33b (boundary side wall) and a boundary side wall 33c that constitute a pair, and extend from the rear wall 33a toward the distal end side of the rigid distal end portion 10 in the longitudinal direction A. The side wall 33b and the side wall 33c have a positional relationship in which they face each other in the width direction C with the central axis X interposed therebetween.

Figure 4:
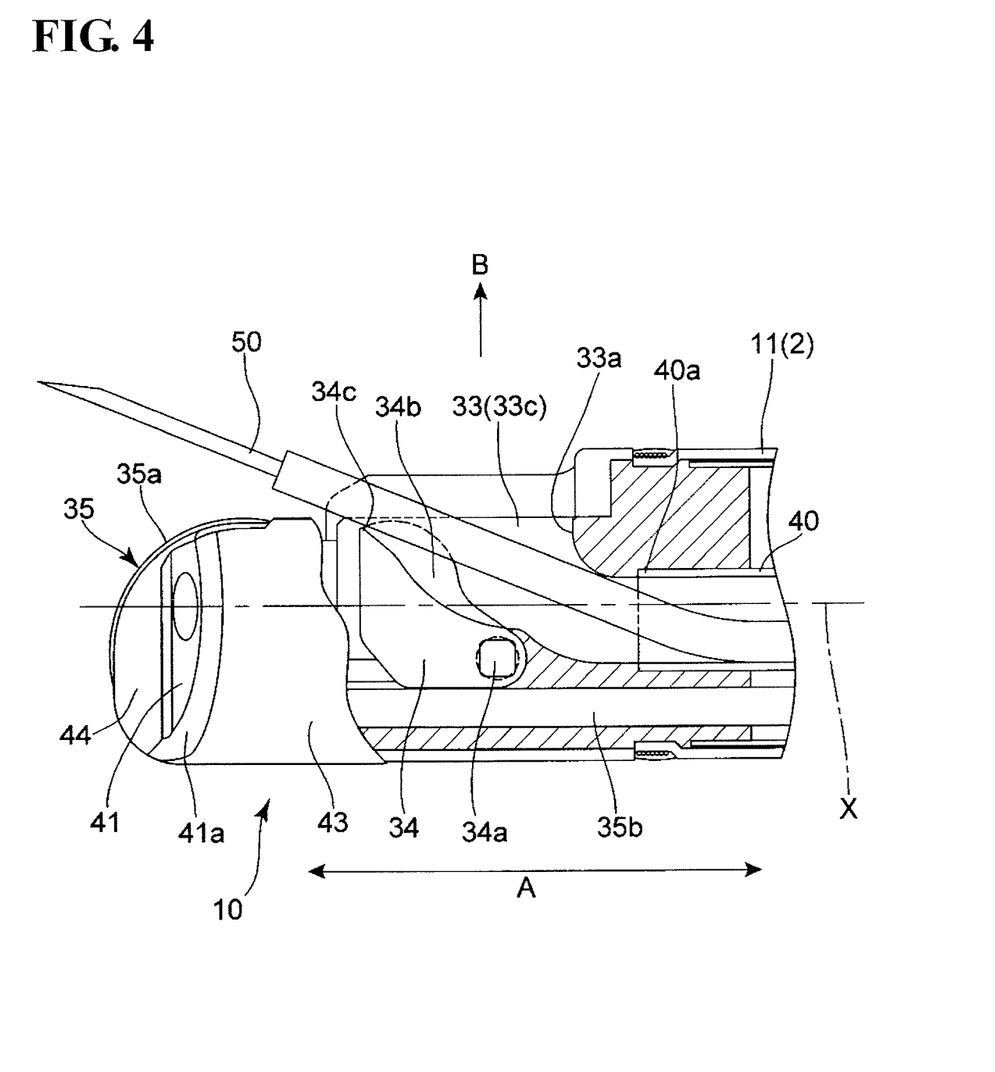
FIG. 4 is a side view of the rigid distal end portion in a state in which a puncture needle protrudes from a laterally open recess, illustrating a part of the rigid distal end portion in a cross-sectional view taken along a line IV-IV of FIG. 3.
Figure 5:
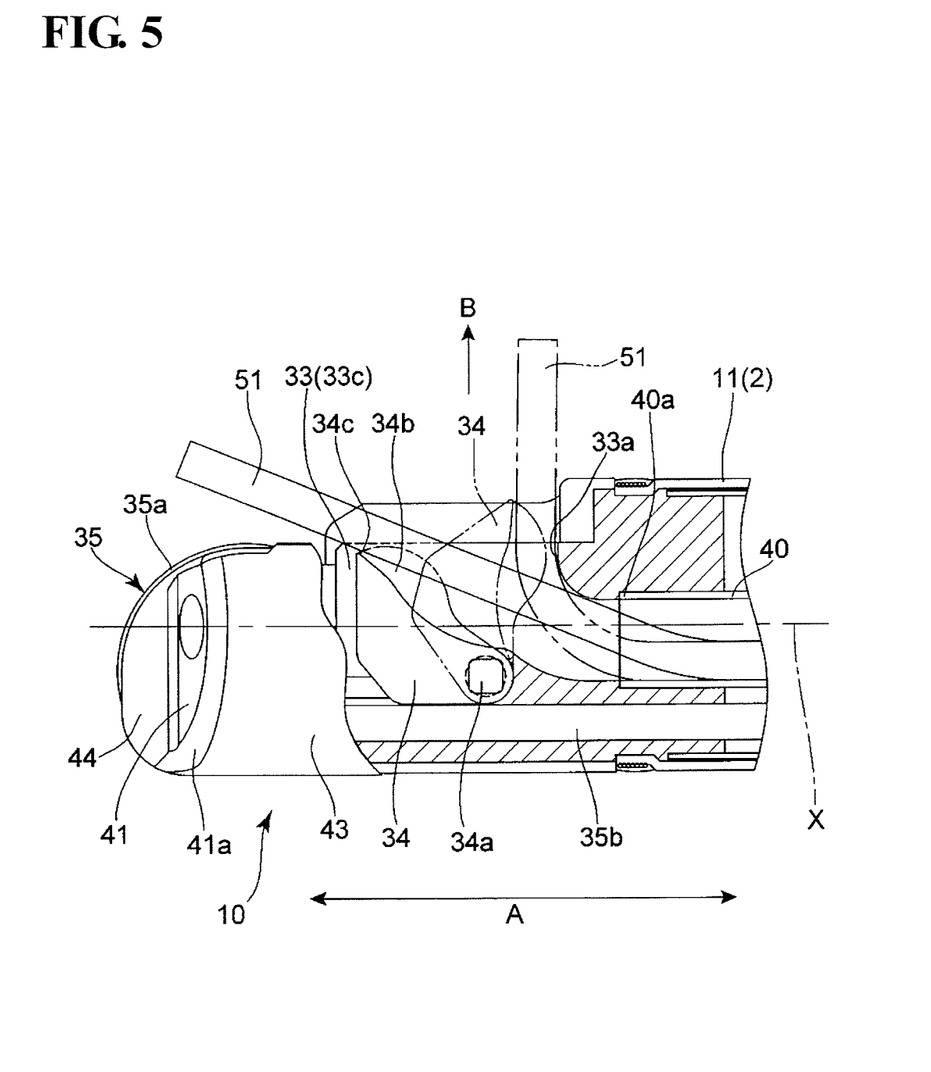
FIG. 5 is a side view like FIG. 4, illustrating the state in which a contrast tube protrudes from the laterally open recess.

The treatment tool conduit 40 (FIGS. 2 to 5) whose rear end is contiguous with the treatment tool insertion opening 23 (FIG. 1) is arranged inside the insertion portion 2 from the operation portion 3, and the distal end connecting portion 40a of the treatment tool conduit 40 that is located at the distal end thereof is in communication with the laterally open recess 33. The rear wall 33a has an opening to which the distal end connecting portion 40a is connected. As shown in FIGS. 3 to 5, the treatment tool conduit 40 is arranged on the central axis X, but the central axis of the treatment tool conduit 40 is offset from the central axis X of the insertion portion 2. The offset of the treatment tool conduit 40 will be described later.

The elevator 34 is supported in the laterally open recess 33 so as to be rotatable about a shaft 34a that extends in the width direction C. The elevator 34 indicated by solid lines in FIGS. 4 and 5 is in an initial angle state in which it is laid on the bottom portion of the laterally open recess 33, and the elevator 34 can be rotated from this initial angle state to a standing state that is shown with a dashed-two dotted line in FIG. 5. The operation portion 3 is provided with rising/falling operation means (not shown) for causing the elevator 34 to rise and fall. The side wall 33c of the laterally open recess 33 is set to have a height such that, even in the state in which the elevator 34 is operated to rise as shown in FIG. 5, the elevator 34 hardly protrudes from the laterally open recess 33 in the observation direction B. The elevator 34 has a V groove 34b whose central part is deeper than both sides in the width direction C. As shown in FIGS. 4 and 5, the V groove 34b is inclined to approach the open surface of the laterally open recess 33 (protrude in the observation direction B), in the initial angle state of the elevator 34, while moving away from the shaft 34a toward the distal end of the rigid distal end portion 10 in the longitudinal direction A, and the distal end part of the V groove 34b serves as a top portion 34c that protrudes the most in the observation direction B. As shown in FIGS. 4 and 5, the flexible linear treatment tools such as the puncture needle 50 and the contrast tube 51 that are inserted into the treatment tool conduit 40 to reach the laterally open recess 33 are supported in the V groove 34b (in particular, in the vicinity of the top portion 34c) of the elevator 34, and the direction in which the flexible linear treatment tools protrude from the laterally open recess 33 is set.

The ultrasonic probe 35 is a convex type ultrasonic probe that includes a wave transmission/reception face (acoustic lens) 35a that is convexly curved, and is provided at the distal end of the rigid distal end portion 10. An ultrasonic signal cable 35b (FIGS. 4 and 5) connected to the ultrasonic probe 35 is guided from the insertion portion 2 to the cable 6 via the operation portion 3, and is connected to a not-shown ultrasonic observation device via the ultrasonic signal connector 7 (see FIG. 1). The ultrasonic probe 35 emits ultrasonic waves to a scan plane that is parallel to the drawing plane of FIGS. 4 and 5 to obtain an ultrasonic tomographic image.

As shown in FIG. 3, the wave transmission/reception face 35a of the ultrasonic probe 35 is offset from the optical observation portion 30 in the width direction C, and is arranged so as to partially overlap the distal end part of the optical observation portion 30 in the longitudinal direction A. In more detail, in the width direction C, the optical observation portion 30 is located on one side (side far away from the central axis X and the treatment tool conduit 40) of the side face 33b of the laterally open recess 33, and the wave transmission/reception face 35a is located on the opposite side of the side face 33b (side on which the central axis X and the treatment tool conduit 40 are located). Furthermore, the arrangement is such that the wave transmission/reception face 35a partially overlaps the side face 33b in the longitudinal axial direction A (a part of the wave transmission/reception face 35a and the side face 33b are parallel to each other in the width direction C). By setting the position of the wave transmission/reception face 35a in this way, it is possible to reduce the length, in the longitudinal direction A, of the rigid distal end portion 10, compared to a configuration in which the entire wave transmission/reception face 35a is offset (i.e., shifted to the left side of the FIG. 3) from the optical observation portion 30 and the laterally open recess 33 in the longitudinal direction A. Note that the wave transmission/reception face 35a of the ultrasonic probe 35 is offset from the elevator 34 in the longitudinal direction A (i.e., the wave transmission/reception face 35a is parallel to the elevator 34 in the longitudinal direction A), and the ultrasonic probe 35 and the elevator 34 are not in the relationship of being parallel to each other in the width direction C, thus making it possible to suppress an increase in the diameter of the rigid distal end portion 10 in the width direction C.

Furthermore, when the rigid distal end portion 10 is viewed from the side in the observation direction B as shown in FIG. 3, the top portion 34c of the elevator 34 is located on a virtual line F that connects a center D of the outer shape (outer shape center D) of the wave transmission/reception face 35a of the ultrasonic probe 35 and a center E in the width direction (width direction center E) of the distal end connecting portion 40a of the treatment tool conduit 40. In more detail, the treatment tool conduit 40 is arranged offset from the central axis X in the width direction C so that the width direction center E of the distal end connecting portion 40a is located closer to the side face 33c of the laterally open recess 33 than to the side face 33b thereof. As described above, the wave transmission/reception face 35a of the ultrasonic probe 35 is arranged closer to the central axis X (closer to the treatment tool conduit 40) than to the side face 33b of the laterally open recess 33, and thus the outer shape center D of the wave transmission/reception face 35a is located closer to the side face 33c than the central axis X. As a result, the virtual line F that connects the outer shape center D and the width direction center E is located closer to the side face 33c than the central axis X. The amounts of offset of the outer shape center D and the width direction center E from the central axis X in the width direction C are equal to each other, and the virtual line F is substantially parallel to the central axis X that extends in the longitudinal direction A. Also, the top portion 34c is located on the virtual line F, by setting the V groove 34b of the elevator 34 to be asymmetric in the width direction C with respect to the central axis X so that the top portion 34c, similar to the outer shape center D and the width direction center E, is offset from the central axis X (the top portion 34c is located closer to the side face 33c than to the side face 33b). By meeting the above-described conditions (positional relationship) of the elevator 34, the ultrasonic probe 35, and the treatment tool conduit 40, it is possible to appropriately position, in the ultrasonic scan plane of the ultrasonic probe 35, the puncture needle 50 (FIG. 4) that was guided from the treatment tool conduit 40 to the top portion 34c of the elevator 34, while achieving the above-described effects of reducing the length of the rigid distal end portion 10.

The rigid distal end portion 10 has an inclined surface 41 and an inclined surface 42 on the two sides in the width direction C of the wave transmission/reception face 35a of the ultrasonic probe 35. On the base end side (bending portion 11 side) relative to the inclined surface 41 and the inclined surface 42, the outer circumferential surface of the rigid distal end portion 10 serves as a cylindrical surface 43 having a substantially constant diameter except for the positions at which the optical observation portion 30 and the laterally open recess 33 are formed. The inclined surface 41 and the inclined surface 42 are surfaces that are inclined to approach the central axis X while moving away from the cylindrical surface 43 toward the distal end side of the rigid distal end portion 10 in the longitudinal direction A. A smoothly curved surface 41*a* is connected (chamfered) between the inclined surface 41 and the cylindrical surface 43, and a smoothly curved surface 42*a* is connected (chamfered) between the inclined surface 42 and the cylindrical surface 43. Due to the presence of the inclined surface 41 and the inclined surface 42, the rigid distal end portion 10 is tapered such that its length in the width direction C gradually decreases toward the distal end side. Also, a most distal end of the rigid distal end portion 10 that is located forward of the inclined surface 41 and the inclined surface 42 is provided with a pair of distal end parallel walls 44 and 45, which are parallel to the central axis X, are separated from each other in the width direction C, and are substantially parallel to each other, on the two sides of the wave transmission/reception face 35*a* of the ultrasonic probe 35, and the length in the width direction C is reduced to a minimum dimension that is constituted only by the width of the wave transmission/reception face 35*a* of the ultrasonic probe 35 and the thicknesses of the distal end parallel walls 44 and 45 on both sides thereof. A peripheral edge portion serving as a smoothly curved surface 44*a* is connected (chamfered) extending from the distal end parallel wall 44 to the inclined surface 41, and a peripheral edge portion serving as a smoothly curved surface 45*a* is connected (chamfered) extending from the distal end parallel wall 45 to the inclined surface 42.

The ultrasonic endoscope 1 having the above-described configuration performs optical observation using the side-viewing optical observation portion 30 via the objective window 31 in a state in which the insertion portion 2 is inserted into a body cavity to cause the rigid distal end portion 10 to reach a target position. When performing endoscopic retrograde cholangiopancreatography (ERCP), the contrast tube 51 that is inserted into the treatment tool conduit 40 from the instrument insertion opening 23 of the operation portion 3 is placed on the V groove 34*b* of the elevator 34 so as to protrude from the laterally open recess 33 as shown in FIG. 5, and the elevator 34 is set to the standing state as shown with the dashed-two dotted line in FIG. 5 to cause the distal end of the contrast tube 51 to be directed in the observation direction B. Then, the contrast tube 51 is inserted into a target part under direct vision with the optical observation portion 30, and X-ray imaging is performed with retrograde injection of a contrast agent.

Furthermore, when performing endoscopic ultrasound-guided fine needle aspiration (FNA), the wave transmission/reception face 35*a* of the ultrasonic probe 35 is brought into contact with an affected part, and emits ultrasonic waves to obtain an ultrasonic tomographic image. By placing the puncture needle 50 inserted from the instrument insertion opening 23 of the operation portion 3 onto the V groove 34*b* of the elevator 34 so that the puncture needle 50 protrudes from the laterally open recess 33 as shown in FIG. 4, the puncture needle 50 is positioned in the vicinity of the ultrasonic probe 35, and it is possible to perform a predetermined treatment. As is clear from FIG. 4, it is the vicinity of the top portion 34*c* of the elevator 34 that is mainly relevant to supporting the puncture needle 50, and the position of the top portion 34*c* affects the accuracy of the position of and the protrusion direction in which the puncture needle 50 protrudes from the laterally open recess 33. As described above, as a result of the top portion 34*c* of the elevator 34 being positioned on the virtual line F that connects the outer shape center D of the wave transmission/reception face 35*a* of the ultrasonic probe 35 and the width direction center E of the distal end connecting portion 40*a* of the treatment tool conduit 40, it is possible to appropriately position, in the ultrasonic scan plane of the ultrasonic probe 35, the puncture needle 50 guided from the treatment tool conduit 40 to the top portion 34*c* of the elevator 34. Furthermore, also when the angle of the elevator 34 is changed with respect to the shaft 34*a*, it is possible to change the protrusion direction while keeping the position of the puncture needle 50 within the ultrasonic scan plane.

In the embodiment shown in FIG. 3, the virtual line F that connects the outer shape center D of the wave transmission/reception face 35*a* of the ultrasonic probe 35 and the width direction center E of the distal end connecting portion 40*a* of the treatment tool conduit 40 is substantially parallel to the central axis X of the insertion portion 2. In other words, the configuration is such that, based on the wave transmission/reception face 35*a* of the ultrasonic probe 35 that is arranged offset to the side wall 33*c* side relative to the center (central axis X), in the width direction C, of the rigid distal end portion 10, the distal end connecting portion 40*a* of the treatment tool conduit 40 and the top portion 34*c* of the elevator 34 are also arranged offset to the side wall 33*c* side in the width direction C.

Figure 6:
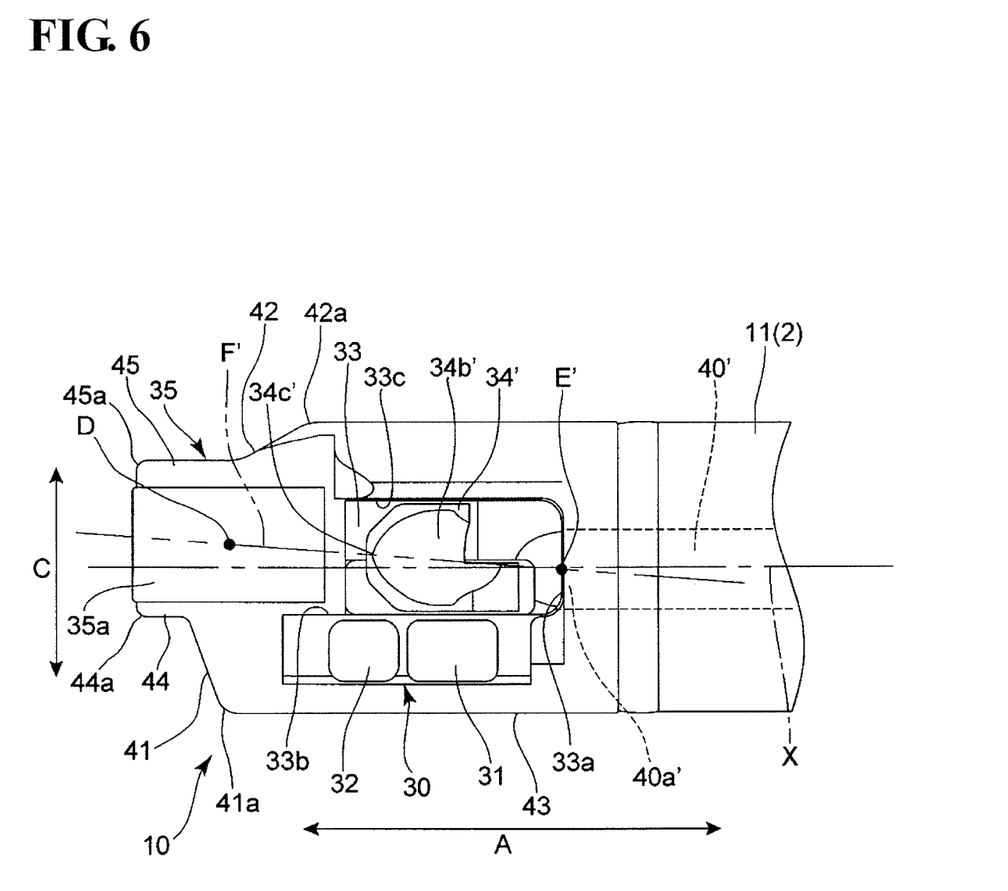
FIG. 6 is a plan view like FIG. 3, illustrating a modification in which the arrangement of constituent components of the rigid distal end portion is different.

FIG. 6 illustrates a modification in which the arrangement of the constituent components of the rigid distal end portion 10 is different from that of FIG. 3. In this modification, while the arrangement of the ultrasonic probe 35 (the position of the outer shape center D of the wave transmission/reception face 35*a*) is the same as in the embodiment of FIG. 3, the positions, in the width direction C, of a treatment tool conduit 40' and a top portion 34*c*' of an elevator 34' are different. When the rigid distal end portion 10 is viewed from the side in the observation direction B as shown in FIG. 6, there is a relationship in which a width direction center E' of a distal end connecting portion 40*a*' of the treatment tool conduit 40' is located on the central axis X, and a virtual line F' that connects the width direction center E' and the outer shape center D of the wave transmission/reception face 35*a* of the ultrasonic probe 35 intersects (is not parallel to) the central axis X that extends in the longitudinal direction A. The top portion 34*c*' located at the distal end of a V groove 34*b*' of the elevator 34' is set at a position in the width direction C that is closer to the side wall 33*b* of the laterally open recess 33 than the top portion 34*c* of the embodiment of FIG. 3, and the top portion 34*c*' is located on the virtual line F'. In the above-described modification of FIG. 6 as well, the puncture needle 50 (see FIG. 4) that extends from the distal end connecting portion 40*a*' of the treatment tool conduit 40' and protrudes by being guided by the top portion 34*c*' of the elevator 34' can appropriately be positioned in the ultrasonic scan plane of the ultrasonic probe 35, and the same effect as the embodiment of FIG. 3 can be achieved. The shape of the outer surface of the rigid distal end portion 10 of FIG. 6 including the inclined surfaces 41 and 42, and the distal end parallel walls 44 and 45 is the same as in the embodiment shown in FIG. 3.

The tapered rigid distal end portion 10 according to the embodiments can have superior insertability when the insertion portion 2 of the ultrasonic endoscope 1 is inserted into a body cavity. In detail, as described above, the most distal end of the rigid distal end portion 10 has the dimension in the width direction C that is within the sum of the width of the wave transmission/reception face 35a of the ultrasonic probe 35 and the thicknesses of the distal end parallel walls 44 and 45 on the two sides thereof (the most distal end has a shape with a small width without portions on the outer sides, in the width direction C, of the distal end parallel walls 44 and 45), and is thus very compact, so that the insertion is unlikely to be hindered. Furthermore, the inclined surface 41 and the inclined surface 42 that are formed in a region contiguous with the most distal end having a small-width function as guide means for helping, with their inclination, the rigid distal end portion 10 be smoothly inserted. In addition, since the peripheral edge portions between the inclined surfaces 41 and 42, and the distal end parallel walls 44 and 45 are chamfered as the smoothly curved surfaces 41a, 42a, 44a, and 45a, there is no risk of catching occurring on the peripheral edge portions.

As described above, the ultrasonic endoscope 1 to which the present invention is applied can use a single ultrasonic endoscope 1 to perform both endoscopic retrograde cholangiopancreatography (ERCP) and endoscopic ultrasound-guided fine needle aspiration (FNA). Also, it is possible to perform reliable ultrasonic diagnostic and treatment by guiding the puncture needle 50 into the ultrasonic scan plane of the ultrasonic probe 35, while achieving downsizing of the rigid distal end portion 10 including the ultrasonic probe 35 in the longitudinal direction A. Accordingly, with a reduction in the length of the rigid distal end portion 10, it is possible to improve the insertability of the insertion portion 2 into an observation target without sacrificing operability.

Furthermore, downsizing in the width direction C is realized in the vicinity of the distal end of the rigid distal end portion 10, due to the formation of the inclined surfaces 41 and 42 and the distal end parallel walls 44 and 45, contributing to a further improvement in the insertability of the insertion portion 2 into an observation target.

Note that, as is clear from FIGS. 3 and 6, the relative positions, in the longitudinal direction A, of the inclined surface 41 and the inclined surface 42 are different, and the inclined surface 41 is located closer to the distal end of the rigid distal end portion 10. Furthermore, the inclined surface 41 has a larger inclination angle with respect to the central axis X extending in the longitudinal direction A than the inclined surface 42. Such differences in the inclination angle and the positions at which the inclined surface 41 and the inclined surface 42 are formed result from the condition that the optical observation portion 30 is provided on the base end side (bending portion 11 side) of the inclined surface 41, and the like. Note that, if structurally possible, it is also possible to employ a configuration in which the inclined surface 41 and the inclined surface 42 are aligned in the longitudinal direction A, or configuration in which the inclined surface 41 and the inclined surface 42 have the same inclination angle with respect to the central axis X, for example.

The present invention has been described above with reference to the illustrated embodiments, but various modifications are possible in portions not essential in the present invention without limiting to the specific configurations shown in the illustrated embodiments.

INDUSTRIAL APPLICABILITY

As described in detail above, in the ultrasonic endoscope of the present invention, at least a part of the wave transmission/reception face of the ultrasonic probe, and a boundary side wall of the laterally open recess are arranged so as to overlap each other in the longitudinal direction of the insertion portion (they are arranged in parallel to each other in the width direction of the insertion portion), making it possible to downsize the rigid distal end portion including the ultrasonic probe in the longitudinal direction. Furthermore, by employing the positional relationship in which the ultrasonic probe and the elevator are not parallel to each other in the width direction of the insertion portion, it is possible to downsize the rigid distal end portion in the width direction. Furthermore, when the rigid distal end portion is viewed from the side in the observation direction, the top portion of the elevator is located on the virtual line that connects the center of the wave transmission/reception face of the ultrasonic probe, and the center, in the width direction, of the distal end connecting portion of the treatment tool conduit, and thus a treatment tool can reliably protrude into the scan plane of the ultrasonic probe. Accordingly, it is possible to realize downsizing of the rigid distal end portion of the ultrasonic endoscope, and excellent operability of the treatment tool, contributing to an improvement in performance of the ultrasonic endoscope.

DESCRIPTION OF REFERENCE SIGNS

1 Ultrasonic endoscope
2 Insertion portion
3 Operation portion
4 Universal tube
5 Video connector
6 Cable
7 Ultrasonic signal connector
10 Rigid distal end portion
11 Bending portion
12 Flexible tube
21 Operation knob
22 Suction button
23 Treatment tool insertion opening
30 Optical observation portion
31 Objective window
32 Illumination window
33 Laterally open recess
33a Rear wall
33b Side wall (boundary side wall)
33c Side wall
34, 34' Elevator
34a Shaft
34b, 34b' V groove
34c, 34c' Top portion
35 Ultrasonic probe
35a Wave transmission/reception face
35b Ultrasonic signal cable
40, 40' Treatment tool conduit
40a, 40a' Distal end connecting portion
41, 42 Inclined surface
41a, 42a Curved surface
43 Cylindrical surface
44, 45 Distal end parallel walls
44a, 45a Curved surface
50 Puncture needle (treatment tool)
51 Contrast tube (treatment tool)
A Longitudinal direction of insertion portion
B Observation direction
C Width direction of rigid distal end portion
D Outer shape center of wave transmission/reception face of ultrasonic probe E, E' Width direction center of distal end connecting portion of treatment tool conduit
F, F' Virtual line
X Central axis of insertion portion

The invention claimed is:

1. An ultrasonic endoscope that is provided with a rigid distal end portion at a distal end of an elongated insertion portion having a main axis extending in a longitudinal direction, the rigid distal end portion comprising:
   an optical observation portion of a side-viewing type in which an objective window is directed to a side in an observation direction that is substantially orthogonal to the longitudinal direction and a width direction;
   an open recess configured to accommodate a distal end connecting portion of a treatment tool conduit inserted in the insertion portion;
   a pair of side walls that are separated from each other by the open recess and in the width direction that is substantially orthogonal to the longitudinal direction and the observation direction, one wall of the pair of side walls comprising a boundary side wall of the optical observation portion;
   an elevator that is supported in the open recess so as to be able to perform rising/falling operation around a shaft directed in the width direction, and sets a direction in which the treatment tool protrudes from the open recess, using a top portion of the elevator that protrudes the most in the observation direction; and
   an ultrasonic probe configured to obtain an ultrasonic tomographic image via a wave transmission/reception face that comes into contact with a part to be observed;
   wherein with respect to the width direction, the objective window is located on one side of the boundary side wall, and the wave transmission/reception face of the ultrasonic probe is located on the opposite side of the boundary side wall, and
   a plane extending in a direction orthogonal to the longitudinal direction passes through the wave transmission/reception face and the boundary side wall, and the wave transmission/reception face and the elevator are offset from each other in the longitudinal direction.

2. The ultrasonic endoscope according to claim 1, wherein in the observation direction, the top portion of the elevator is located on a virtual line that is substantially parallel to the longitudinal direction and that connects a center of the wave transmission/reception face and a center, in the width direction, of the distal end connecting portion of the treatment tool conduit.

3. The ultrasonic endoscope according to claim 1, wherein in the observation direction, the top portion of the elevator is located on a virtual line that intersects the longitudinal direction and that connects a center of the wave transmission/reception face and a center, in the width direction, of the distal end connecting portion of the treatment tool conduit.

* * * * *